United States Patent [19]

Fenkner et al.

[11] 4,387,596

[45] Jun. 14, 1983

[54] METHOD OF AND DEVICE FOR ULTRASONICALLY TESTING SPHERICAL BODIES

[75] Inventors: Max Fenkner, Schweinfurt; Hilmar Wehner, Schwebheim, both of Fed. Rep. of Germany

[73] Assignee: FAG Kugelfischer Georg Schäfer & Co., Schweinfurt, Fed. Rep. of Germany

[21] Appl. No.: 231,217

[22] Filed: Feb. 2, 1981

[30] Foreign Application Priority Data

Feb. 5, 1980 [DE] Fed. Rep. of Germany ....... 3004079

[51] Int. Cl.³ .................. G01N 29/00; G01M 13/00; G01H 1/00
[52] U.S. Cl. .......................... 73/593; 73/640; 73/660
[58] Field of Search ............... 73/640, 641, 593, 660

[56] References Cited

U.S. PATENT DOCUMENTS

| | | | |
|---|---|---|---|
| 3,183,709 | 5/1965 | Rankin et al. | 73/641 X |
| 3,837,202 | 9/1974 | Hetherington et al. | 73/640 |
| 4,099,418 | 7/1978 | Bennett et al. | 73/641 X |
| 4,281,548 | 8/1981 | Köber | 73/593 |

FOREIGN PATENT DOCUMENTS 2535019 2/1977 Fed. Rep. of Germany ........ 73/593

OTHER PUBLICATIONS

Ultrasound Tests Ball Bearings; Ultrasonics, Nov. 1973, p. 247, by Hoffman Pollard Ltd., Gloucestershire, U.K.
Chapter 23 of a book titled "Ultrasonic Testing of Materials" by Krautkrämer, 2nd Edition, Springer Verlag 1977.

*Primary Examiner*—Anthony V. Ciarlante
*Assistant Examiner*—David V. Carlson
*Attorney, Agent, or Firm*—Karl F. Ross

[57] ABSTRACT

Spherical bodies, such as bearing balls, are tested for machining irregularities or structural defects by subjecting them to supersonic vibrations from two or more ultrasound generators through the intermediary of a coupling liquid in which these bodies are immersed. One ultrasound generator has an axis in line with the body being tested while the other generator or generators have axes including acute angles with the radial directions of that body. The body is subjected to rotation in different planes by injecting the coupling liquid, alternately or simultaneously but at varying relative rates, through two different nozzles into an interspace separating the body from a spherically concave supporting surface.

4 Claims, 2 Drawing Figures

METHOD OF AND DEVICE FOR ULTRASONICALLY TESTING SPHERICAL BODIES

FIELD OF THE INVENTION

Our present invention relates to a device for the testing of spherical bodies, such as ball bearings, with the aid of supersonic waves.

BACKGROUND OF THE INVENTION

The nondestructive testing of solids with the aid of ultrasonics is of relatively recent origin. Reference in this connection may be made, for example, to an article by Byron E. Leonard and C. Gerald Gardner in a survey titled NONDESTRUCTIVE TESTING, NASA SP-5113, published 1973 by the Technology Utilization Office of National Aeronautics and Space Administration, pp. 27ff. An evaluation system using a transducer for emitting the supersonic waves and detecting their echoes is diagrammatically illustrated in FIGS. 3-19 on page 36 of the publication.

In commonly owned German printed specification No. 25 35 019, laid open Feb. 10, 1977, there has been disclosed a technique of ultrasonically testing spherical bodies with the aid of a support forming a spherically concave seating surface in which a body to be tested is cradled, the support and the body under test being immersed in a coupling liquid which forms a film or cushion between the body and its seat; an ultrasound generator disposed below the support emits waves through the latter and the film of coupling liquid toward the center of the body which is also the center of curvature of its seat. The body is rotated during the test by one or more nozzles trained substantially tangentially upon its nadir, i.e. upon the lowest point of the interspace separating it from the support.

While the system described in the German specification operates generally satisfactorily in many instances, we have found that it does not uniformly respond to flaws in the interior and near the surface of the tested body.

We attribute this shortcoming to the fact that the system is most responsive to echoes from the interior of the body and is less sensitive to those originating near its surface.

It has already been proposed to explore the structure of a test body at or near its surface with the aid of several relatively offset ultrasound generators; see the magazine ULTRASONICS of November 1973, pp. 247 and 249. This, however, does not solve the problem of nonuniform sensitivity to structural defects at different depths.

OBJECT OF THE INVENTION

The object of our present invention, therefore, is to provide a simple testing device designed to detect flaws throughout the spherical body with a substantially uniform degree of responsiveness.

SUMMARY OF THE INVENTION

In accordance with our present invention, a spherical body cradled in a spherically concave seating surface of slightly larger radius of curvature through the intermediary of a cushion of coupling liquid, as taught by German printed specification No. 25 35 019 referred to above, is tested by ultrasonic waves transmitted to the body through the coupling liquid in one direction of propagation passing through the center of the body and in at least one other direction of propagation offset from that center within the body. At the same time the body is subjected to successive rotation in at least two different planes (i.e. about as many different axes passing through its center) while the received echoes are evaluated in a manner well known per se.

Advantageously, pursuant to a more particular feature of our invention, the rotation of the body under test in two or more planes—specifically about several horizontal axes—is brought about by injecting the coupling liquid into the interspace between the body and its seating surface from at least two different directions substantially tangential to the body. When injection in these directions takes place at different times, the plane of rotation changes abruptly; with simultaneous injections at relatively varying rates, on the other hand, a gradual displacement of the axis and the plane of rotation can be achieved.

Thus, a device embodying our invention method comprises first ultrasound-generating means trained through a supporting member and a cushion of coupling liquid upon the center of curvature of a spherically concave recess of that member and second ultrasound-generating means trained through the support member and the cushion upon the body to be tested along one or more lines offset from that center of curvature. Drive means for setting the body in successive rotation about two or more different axes, as discussed above, may comprise a plurality of nozzles for injecting the coupling liquid into the recess at different angles.

BRIEF DESCRIPTION OF THE DRAWING

The above and other features of our invention will now be described in detail with reference to the accompanying drawing in which.

SPECIFIC DESCRIPTION

Figure 1:
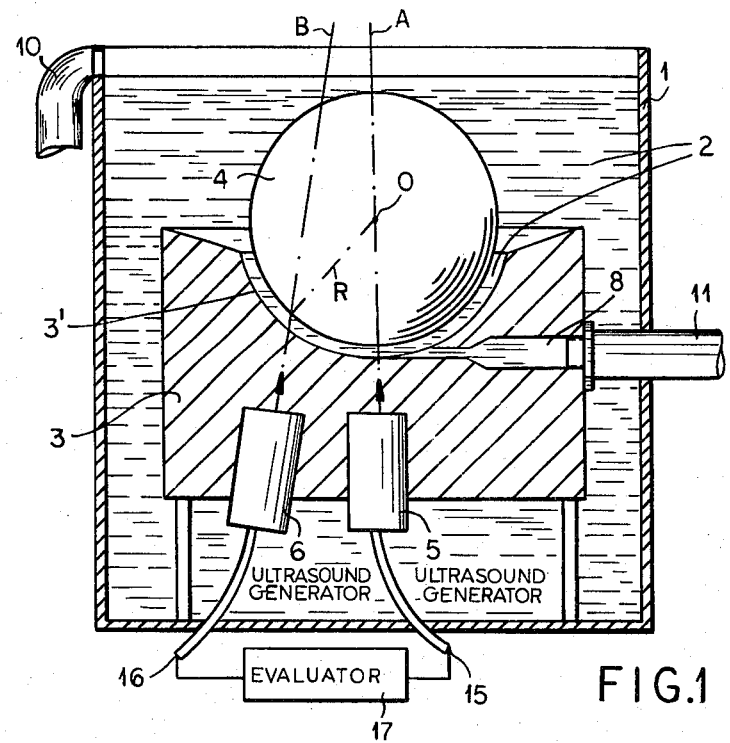
FIG. 1 is a partly diagrammatic sectional elevational view of a testing device embodying our invention.

In the drawing we have shown an upwardly open vessel 1 surrounding a support member 3 which is formed with a spherically concave seating surface 3' for a metal ball 4 of slightly smaller radius R to be tested.

Figure 2:
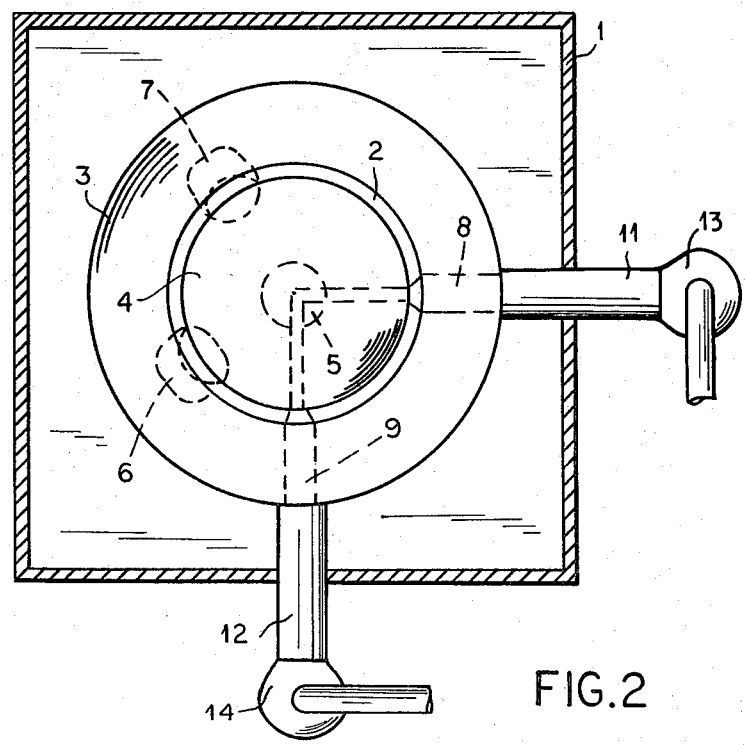
FIG. 2 is a top view of the device of FIG. 1.

Ball 4 is concentrically supported on its seat 3' by a film of coupling liquid 2 (e.g. a mixture of glycerol, water and a wetting agent) which fills the container 1 to a level above the top of the ball; in FIG. 2 the liquid has been omitted for the sake of clarity.

Three ultrasound generators 5, 6 and 7 (the last one shown only in FIG. 2) are inserted from below into the support 3 to transmit ultrasonic waves to ball 4 in different directions, i.e. along lines A and B in the case of generators 5 and 6, respectively. It will be noted that the direction of propagation A passes directly through the center of curvature O of seat 3' whereas the direction B includes an acute angle with the radius at the point of incidence.

Two nozzles 8 and 9 extend horizontically at right angles to each other into support 3 to inject coupling liquid from respective conduits 11 and 12 into the interspace between seat 3' and ball 4, the nozzles opening into the recess 31 substantially at its nadir.

Pumps 13 and 14 can be operated alternately, or concurrently at relatively varying feed rates, to set the ball 4 in rotation about different horizontal axes as already described. An overflow port 10 above the level of ball 4 returns excess liquid to a nonillustrated reservoir.

Leads 15 and 16 from transducers 5 and 6, as well as a similar lead (not shown) from transducer 7, extend to a conventional evaluator 17 comprising, for example, an oscilloscope for visually displaying any detected flaws.

Transducer 7, spaced from a vertical centerline of member 3 by approximately the same distance as transducer 6, may have an axis inclined to the vertical at such an angle that the three ultrasound generators explore the ball 4 at different depths.

We claim:

1. A device for ultrasonically testing spherical bodies, comprising:
    a supporting member with a spherically concave recess accommodating a body to be tested;
    a supply of coupling liquid communicating with said recess for providing a cushion of said liquid between said member and a body seated in said recess;
    first ultrasound-generating means trained vertically from below through said member and said cushion upon the center of curvature of said recess;
    second ultrasound-generating means trained inclinedly from the vertical at an angle less than 90° from below through said member and said cushion upon a body seated in said recess along at least one line offset from said center of curvature;
    drive means for setting a body to be tested in successive rotation about at least two different axes substantially passing through said center of curvature; and
    evaluating means connected to said first and second ultrasound-generating means.

2. A device as defined in claim 1 wherein said second ultrasound-generating means comprises a plurality of ultrasound generators equispaced from a vertical centerline of said recess and inclined at different angles to the vertical.

3. A device as defined in claim 1 or 2 wherein said drive means comprises a plurality of nozzles connected to said supply for injecting said coupling liquid into said recess at different angles.

4. A device as defined in claim 3, further comprising a vessel surrounding said member and extending sufficiently high above said recess to enable a body seated therein to be completely immersed in coupling liquid overflowing said recess.

* * * * *